United States Patent [19]

Drent et al.

[11] Patent Number: 5,780,684
[45] Date of Patent: Jul. 14, 1998

[54] HYDROFORMYLATION REACTIONS

[75] Inventors: Eit Drent; Willem Wabe Jager. both of Amsterdam, Netherlands

[73] Assignee: Shell Oil Company. Houston, Tex.

[21] Appl. No.: 783,966

[22] Filed: Jan. 15, 1997

[30] Foreign Application Priority Data

Jan. 16, 1996 [EP] European Pat. Off. ............ 96200100

[51] Int. Cl.$^6$ ................................................. C07C 45/50
[52] U.S. Cl. ................................. 568/454; 568/451
[58] Field of Search ................................. 568/451, 454

[56] References Cited

U.S. PATENT DOCUMENTS

| | | | |
|---|---|---|---|
| 4,960,926 | 10/1990 | Drent | 560/233 |
| 5,210,280 | 5/1993 | Drent | 560/204 |

FOREIGN PATENT DOCUMENTS

| | | | |
|---|---|---|---|
| 0106379 | 4/1984 | European Pat. Off. | C07C 51/14 |
| 0495548 | 7/1992 | European Pat. Off. | C07C 51/14 |
| 95/03269 | 2/1995 | WIPO | C07C 67/38 |
| WO 95/05354 | 2/1995 | WIPO . | |
| 95/30680 | 11/1995 | WIPO | C07F 9/655 |

OTHER PUBLICATIONS

Polyhedron;vol. 9, #9; pp. 1235–1236, 1990.
Journal of Chemical Society;Chem.Commun.; #3; pp. 146–147, 1987.

*Primary Examiner*—Gary Geist
*Assistant Examiner*—Sreeni Padmanabhan
*Attorney, Agent, or Firm*—Dennis V. Carmen

[57] ABSTRACT

The invention relates to a process for hydroformylating olefins with carbon monoxide and a hydrogen atom source in the presence of a catalyst system obtainable by combining (a) a source of a Group VIII metal cation, (b) a compound acting as bidentate ligand of the formula $R^1R^2M^1$—R—$M^2R^3R^4$, wherein $M^1$ and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups, and (c) a source of anions; wherein the hydrogen atom source comprises water or a primary or secondary alcohol.

27 Claims, No Drawings

HYDROFORMYLATION REACTIONS

1. FIELD OF THE INVENTION

The invention relates to hydroformylation reactions. More in particular, the invention relates to hydroformylation reactions conducted in the presence of a homogeneous catalyst system.

2. BACKGROUND OF THE ART

Hydroformylation reactions are known in the art. For instance, "New Synthesis With Carbon Monoxide", edited by J. Falbe (1980) discloses in chapter 1 a multitude of catalyst systems based on Group VIII metals that convert (functionally substituted) olefins with carbon monoxide and hydrogen gas into (functionally substituted) aldehydes or alcohols. The list of references at the end of this chapter runs to almost 2000.

In view of the fact that hydrogen gas is not always available, or available in sufficient quantities, it would be desirable to be able to rely on a process that can be carried out with an alternative hydrogen atom source instead of, or in addition to the hydrogen gas. Unfortunately, no such teaching is provided in the textbook mentioned above.

3. SUMMARY OF THE INVENTION

The present invention aims at providing a process that can be conducted with an alternative hydrogen atom source instead of, or in addition to the hydrogen gas. Accordingly, it provides a process for hydroformylating olefins with carbon monoxide and a hydrogen atom source in the presence of a catalyst system obtainable by combining (a) a source of a Group VIII metal cation, (b) a compound acting as bidentate ligand of the formula $R^1R^2M^1$—R—$M^2R^3R^4$, wherein $M^1$ and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups, and (c) a source of anions; wherein the hydrogen atom source comprises water or a primary or secondary alcohol.

4. DETAILED DESCRIPTION OF THE INVENTION

Use of water or an alcohol in carbonylation reactions is well known. For example, hydroxycarbonylation of ethene yields propionic acid. Likewise, hydroesterification of 1-octene with carbon monoxide and methanol or ethanol yields methyl respectively ethyl nonanoate. Such processes are disclosed, for instance, in European patent application Nos. 106,379; 274,795; 495,547 and 495,548. It is hence quite surprising that a hydroformylation product rather then a carbonylation product is formed.

A possible explanation for this phenomenon is that the catalyst system of the present invention, in contrast to those of the prior art, converts part of the carbon monoxide and water into molecular hydrogen and carbon dioxide. In case an alcohol such as isopropanol is used, then an aldehyde or ketone (acetone) is produced. Meanwhile, the molecular hydrogen together with carbon monoxide reacts with the olefin to form the hydroformylation product. This hypothesis appears valid as carbon dioxide is formed in the reaction with water. However, no free hydrogen gas is found upon termination of the reaction. Moreover, acetylenically unsaturated compounds (e.g., phenyl ethyne and 1-pentyne) are carbonylated rather than hydroformylated in the presence of the catalyst system of the present invention (cf. International application No. WO 95/03269).

The alternative hydrogen atoms source is suitably a relatively cheap primary or secondary alcohol, e.g., ethanol, i-propanol, etc., having up to 8 carbon atoms. However, alcohols even up to 16 carbon atoms may be used. More preferably, water is used.

Hydroformylation may also be carried out in the presence of added hydrogen gas. The amount thereof may vary within wide ranges. In typical preparations of synthesis gas, which is the likely source of the carbon monoxide, the molar ratio of hydrogen gas versus CO is roughly 2. This synthesis gas can be used as such, or after (partial) depletion of the hydrogen gas.

It will be appreciated that proper selection of the process conditions is of particular relevance. Accordingly, the process is suitably carried out at a temperature in the range of 100° to 200° C., preferred temperatures being in the range of 120° to 180° C. The reaction pressures may vary more widely. For instance, the reaction can be carried out with pressures in the range of 1 to 200 bar gauge, pressures in the range of 5 to 60 bar gauge being preferred.

Carbon monoxide and the alternative hydrogen atom source are preferably supplied in molar excess over the olefin. Preferably they are supplied in a molar ratio CO versus hydrogen atom source within the range of 10:1 to 1:10, preferably within the range of 5:1 to 1:5, more preferably within the range of 2:1 to 1:2.

In the present specification, Group VIII metals (referring to the Periodic Table of the Elements as disclosed in the 61st ed. of the Handbook of Chemistry and Physics) comprise the elements Fe, Co, Ni, Ru, Rh, Pd, Os, Ir and Pt. Preferably the Group VIII metal is a platinum group metal, i.e., Ni, Pd or Pt. Of these, palladium is most preferred.

Examples of suitable sources of the cation are salts, such as salts of the Group VIII metal and nitric acid, sulphuric acid, carboxylic acids having up to 12 carbon atoms in the carboxylate group or sulphonic acid; and metal complexes, e.g., with carbon monoxide or acetylacetonate. Palladium (II) acetate is an example of a suitable source of the cation.

Regarding the bidentate ligand constituting component (b) of the catalyst system, $M^1$ and $M^2$ preferably both represent phosphorus atoms. The bivalent bridging group R typically is an organic group, inclusive organometallic groups such as ferrocylene as in WO 95/06027 or ortho-anellated annular systems as in WO 95/30680, connecting the atoms $M^1$ and $M^2$ through carbon atoms. Usually all bridging atoms are carbon atoms, optionally with heteroatoms atoms (other than H or C) thereto attached. Preferably, R represents an alkylene group containing from 1 to 3 carbon atoms in the bridge, in particular an ethylene group.

The bivalent substituted or non-substituted group, represented by $R^1$ together with $R^2$, preferably contains from 5 to 9 atoms, preferably 8 atoms. Examples of suitable bivalent groups are 1,6-hexylene, 1,6-heptylene, 1,5-octylene, etc. Together with $M^1$, this group forms a phosphacycloalkyl group. Preferably, $R^1$ together with $R^2$ represent a bivalent substituted or non-substituted cyclic group. Together with $M^1$, this preferred group forms a phosphabicycloalkyl group. Examples of suitable bivalent cyclic groups are 1,4-cyclohexylene, 1,4-cycloheptylene, 1,2-cyclooctylene, 1,4-cyclooctylene, 1,5-cyclooctylene and 2-methyl-1,5-cyclooctylene groups.

$R^3$ and $R^4$ may independently represent any substituted or non-substituted hydrocarbyl group, such as alkyl, aryl, alkaryl or aralkyl groups. Preferably, $R^3$ and $R^4$ together have the same meaning as $R^1$ together with $R^2$.

Suitable substituents in case any of R, or $R^1$ to $R^4$ is substituted may be selected from the group consisting of halogen atoms, and cyano, alkoxy, amino and alkylamino groups. The alkyl groups in the alkoxy and alkylamino groups preferably each contain from 1 to 4 carbon atoms.

Particularly preferred bidentate ligands are the [3,3,1] and [4,2,1] isomers of 1,2-P,P'-bis(9-phosphabicyclononyl) ethane, 1,2-P,P'-bis(dimethyl-9-phosphabicyclononyl) ethane, 1,3-P,P'-bis(9-phosphabicyclononyl)propane, 1,3-P, P'-bis(dimethyl-9-phosphabicyclononyl)propane.

For the preparation of the bidentate ligands, reference is made to known techniques, for example the method disclosed in British patent application No. 1,127,965 and Canadian patent application No. 2,086,285.

The catalyst systems used in the process of the invention are further based on a source of anions, i.e., component (c). It is believed that the size of the anion and the distribution of electric charge in the anion significantly contribute to the stability of the catalyst system. Suitably, acids are used as the source of anions, or the salts thereof. Preferably, anions are used that are the conjugated base of acids having a pKa (measured at 18° C. in water) of less than 3, preferably less than 2. The anions derived from these acids are non-coordinating or weakly coordinating with the Group VIII metal cation, by which is meant that little or no covalent interaction occurs between the anion and the cation. Catalysts based on these anions have a substantially improved activity.

Suitable anions include anions derived from Bronsted acids, such as from phosphoric acid and sulphuric acid, and in particular from sulphonic acids and (halogenated) carboxylic acids, such as trifluoroacetic acid, 2,6-dichlorobenzoic acid, and 2,6-bis(trifluoromethyl)benzoic acid or trifluoroacetic acid, etc. Anions derived from sulphonic acids are particularly preferred, for example methanesulphonic acid, trifluoroethanesulphonic acid, tert-butanesulphonic acid, p-toluenesulphonic acid and 2,4,6-trimethylbenzenesulphonic acid.

Also, complex anions are suitable, such as the anions generated by a combination of a Lewis acid such as $BF_3$, $B(C_6F_5)_3$, $AlCl_3$, $SnF_2$, $Sn(CF_3SO_3)_2$, $SnCl_2$ or $GeCl_2$, with a protic acid, preferably having a pKa of less than 5, such as a sulphonic acid, e.g. $CF_3SO_3H$ or $CH_3SO_3H$ or a hydrohalogenic acid such as HF or HCl, or a combination of a Lewis acid with an alcohol. Examples of such complex anions are $BF_4^-$, $SnCl_3^-$, $[SnCl_2.CF_3SO_3]^-$ and $PF_6^-$.

The quantity in which the catalyst system is used, is not critical and may vary within wide limits. Usually amounts in the range of 10–8 to 10–1, preferably in the range of 10–7 to 10–2 mole atom of component (a) per mole of olefin are used.

For the preparation of the catalyst systems of the invention, the amount of bidentate ligand is generally applied in some excess of the amount of the Group VIII metal cation, expressed as moles of bidentate ligand per mole atom of the cation. Typically the amount of bidentate ligand is selected such that per mole atom of the cation 0.5 to 10 moles of bidentate ligand are present. The active species, however, is believed to be based on an equimolar amount of bidentate ligand per mole cation. Thus, the molar amount of bidentate ligand per mole of cation is preferably in the range of 1 to 3, more preferably in the range of 1 to 2. In the presence of oxygen, slightly higher amounts may be beneficial. The amount of the anion source may range from 0.5 to 15, preferably from 1 to 8 moles per mole of cation.

Preferably, the catalyst system includes halide anions in a substochiometric amount, i.e., less than 3:1, preferably less than 1:1, for instance from 0.02:1 to 1:1, per mole of cation.

The olefins used for hydroformylation typically have from 2 to 40 carbon atoms per molecule. They may comprise one or more double bonds per molecule. Preferred are internal olefins having from 6 to 30 carbon atoms, or mixtures thereof. Linear internal C6 to $C_8$ olefins, and linear internal $C_{10}$ to $C_{14}$ olefins are commercially readily available, for example as products of a process for the oligomerization of ethylene, followed by a double bond isomerization and disproportionation reaction. In the process of the invention, these (mixtures of) internal olefins can be hydroformylated at high rates and at almost complete conversion.

Substituted olefins may also be used, for example unsaturated carboxylic acids, esters of such acids, or unsaturated esters of carboxylic acids, e.g. allylacetate.

If desired, branched olefins such as propene trimer or isomeric butene dimers ("DIMERSOL" a trademark) may be used, but the hydroformylation product will then, of course, contain branched structures as well.

Also, olefinically unsaturated polymeric feedstock, such as atactic polyolefins like 'Shube's' (mixture of oligomers of $C_{16}$-olefins), "NAPVIS" and "HYVIS" (trademarks for low molecular weight polyisobutylene) and styrene-butadiene (block)copolymers may be converted into interesting alcohols (as intermediates to synthetic lubricants, functionalized additives, etc.).

Finally, alpha-olefins, such as 1-octene and propene, and diolefins, such as norbornadiene, dicyclopentadiene, 1,5-hexadiene and 1,7-octadiene may be used. The diolefins will of course yield (predominantly) a di-hydroformylated product, although also mono-hydroformylated products may be formed.

The inventors have found that in the presence of water and an acid as anion source it is also possible to generate the olefin in situ, using an alcohol (other than methanol or an aromatic alcohol), or a precursor thereof (in the form of an ester, an ether or a carbonyl compound) as olefin source. In view of their ease of dehydration, secondary and tertiary alcohols (or their precursors) are preferred. Surprisingly, this provides for an elegant process for preparing primary alcohols from secondary or tertiary alcohols. This process resembles homologation, but does not require a primary alcohol as feedstock. Typical examples include alcohols having 3 to 20 carbon atoms, such as 2-butanol and 3-hexanol (resulting in the production of 1-pentanol and 1-heptanol respectively). Suitable precursors include compounds such as butanone, diisobutyl ether, isopropyl acetate, etc. In case of a carbonyl compound (in particular a ketone), the reaction is preceded by a hydrogenation reaction wherein the water and carbon monoxide may act as hydrogenation reagent as well.

In the process of the invention, the starting materials and the formed hydroformylation products may act as reaction diluent. Hence, the use of a separate solvent is not necessary. Conveniently, however, the hydroformylation reaction may be carried out in the additional presence of a solvent. As such, saturated hydrocarbons, e.g. paraffins and isoalkanes are recommended and furthermore ethers such as 2,5,8-trioxanonane (diglyme), diethylether and anisole, and ketones, such as methylbutylketone. In case an ether or ketone is used, however, one should be careful to consider that at prolonged reaction conditions, i.e., upon depletion of the olefin feedstock, they may partake in the reaction as discussed above.

The invention will now be further described with reference to the following examples, however, without restricting its scope. The abbreviations used in the Tables have the following meanings:

BCPE=1,2-P,P'-bis(9-phosphabicyclo[3.3.1 or 4.2.1]octyl)ethane
BCPP=1,3-P,P'-bis(9-phosphabicyclo[3.3.1 or 4.2.1]octyl)propane
BIPP=1,3-bis(sec-butylphosphino)propane
BBPE=1,2-bis(sec-butylphosphino)ethane
BBPP=1,3-bis(tert-butylphosphino)propane
MSA=methanesulphonic acid
tBSA=tert-butanesulphonic acid
TFSA=trifluoromethanesulphonic acid
TMBA=2,4,6-trimethylbenzoic acid
EH=2-ethyl-1-hexanol

EXAMPLES 1–16

The experiments were carried out in a magnetically stirred 250 ml autoclave. The autoclave was charged with 20 ml of olefin (1-octene or an internal tetradecene), 5 ml of water, solvent in the amount listed in the table, 0.25 mmol of palladium(II) acetate, 0.6 mmol of bisphosphine ligand and 1 mmol of acid (MSA or TFSA). After being flushed, the autoclave was pressurized with carbon monoxide to a pressure of 40 bar. Subsequently, the reactor was sealed and the contents were heated to a temperature of approximately 150° C. and maintained at that temperature until the reaction was substantially complete. After cooling, a sample was taken from the contents of the reactor and analyzed by Gas Liquid Chromatography. Further details and the results of the analysis can be found in Tables 1 and 2.

The calculated conversion rate is expressed as moles of product per mole atom of palladium and per hour, (mol/mol.h).

Byproducts in the event selectivity towards the alcohol was less than 100%, i.e., using 1-octene, comprised nonyl octanoates, octane carboxylic acids and traces of dioctyl ketones.

COMPARATIVE EXAMPLES A to C

Experiments were carried out in a similar fashion is above, taking into consideration the disclosures of European patent applications Nos. 495,547 (Comparative Example A) and 495,548 (Comparative Example B). Further details and the analytical results are compiled in Table 1.

EXAMPLE 17

An experiment was carried out in a similar fashion is above, with 1-octene as reactant and using 50 ml of s-butanol instead of water. Further details and the analytical results are compiled in Table 2. Byproducts now also comprised butanone.

EXAMPLE 18

The experiment was carried out in a magnetically stirred 250 ml autoclave. The autoclave was charged with 50 ml of 2-butanol, 5 ml of water, 0.25 mmol of palladium(II) acetate, 0.6 mmol of BCPE, 5 mmol MSA and 0.1 mmol HCl. After being flushed, the autoclave was pressurized with carbon monoxide to a pressure of 40 bar. Subsequently, the reactor was sealed and the contents were heated to a temperature of approximately 150° C. and maintained at that temperature for 10 hours. After cooling, a sample was taken from the contents of the reactor and analyzed by Gas Liquid Chromatography. The 2-butanol conversion and linearity of the produced (1-) pentanol was found to be 10% (on the feed), respectively 75% (on the product).

EXAMPLE 19

The experiment of Example 18 was repeated, using 10 ml of water. The 2-butanol conversion and linearity of the produced (1-) pentanol was found to be 25% (on the feed), respectively 70% (on the product).

EXAMPLE 20

The experiment of Example 18 was repeated, however using 30 ml of 3-hexanol, 10 ml of water and a temperature of 155° C. The 3-hexanol conversion and linearity of the produced (1-) heptanol was found to be 15% (on the feed), respectively 70% (on the product).

TABLE 1

| Example No. | Reactant | Ligand | Anion Source (mmol) | Solvent (ml) | Rate (mol/mol · h) | Product(s) Selectivity (%) |
| --- | --- | --- | --- | --- | --- | --- |
| 1 | 1-$C_8$= | BCPP | MSA (1.0) | diglyme (50) | 90 | $C_9$-alcohols (27) |
| 2 | 1-$C_8$= | BCPP | MSA (1.0) HI (0.1) | diglyme (50) | 130 | $C_9$-alcohols (53) |
| 3 | 1-$C_8$= | BCPP | MSA (1.0) HCl (0.1) | diglyme (50) | 80 | $C_9$-alcohols (55) |
| 4 | 1-$C_8$= | BCPP | MSA (1.0) HCl (0.2) | diglyme (50) | 150 | $C_9$-alcohols (61) |
| 5 | 1-$C_8$= | BCPE | MSA (1.0) HCl (0.2) | diglyme (50) | 280 | $C_9$-alcohols (88) |
| 6 | 1-$C_8$= | BCPE | TFSA (1.0) HCl (0.2) | diglyme (50) | 100 | $C_9$-alcohols (90) |
| 7 | 1-$C_8$= | BCPE | TFSA (1.0) HCl (0.2) | EH (25) sulfolane (5) | 110 | $C_9$-alcohols (66) |
| 8 | 1-$C_8$= | BCPE | TFSA (1.0) HCl (0.2) | EH (25) sulfolane (5) | 120 | $C_9$-alcohols (71) |
| 9 | 1-$C_8$= | BCPE | TFSA (1.0) HCl (0.2) | diglyme (40) | 140 | $C_9$-alcohols (93) |
| A | 1-$C_8$= | BIPP | TMBA (10) | ethanol (40) | (100) | ethyl nonanoate |
| B | 1-$C_8$= | BBPP | tBSA (1.0) | methanol (50) | (100) | methyl nonanoate |
| C | 1-$C_8$= | BBPE | MSA (1.0) | diglyme (40) | (100) | nonanoic acid |

TABLE 1-continued

| Example No. | Reactant | Ligand | Anion Source (mmol) | Solvent (ml) | Rate (mol/mol · h) | Product(s) Selectivity (%) |
|---|---|---|---|---|---|---|

Comparative Example A is Example 37 of European patent application No. 495,547 (50 bar, 135° C.); Comparative Example B is Example VI of European patent application No. 495,548 (40 bar, 65° C., in the presence of 5 ml trimethylorthoformate), and Comparative Example C is carried out at the conditions of Example 1 of the present application. The rate for these Comparative Examples is the rate of the carbonylation reaction.

TABLE 2

| Example No. | Reactant | Ligand | Anion Source (mmol) | Solvent (ml) | Rate (mol/mol · h) | Product(s) Selectivity (%) |
|---|---|---|---|---|---|---|
| 10 | $iC_{14}=$ | BCPE | MSA (1.0) HCl (0.2) | EH (25) sulfolane (5) | 189 | $C_{15}$-alcohols (>99) |
| 11 | $iC_{14}=$ | BCPE | MSA (1.0) HCl (0.1) | EH (25) sulfolane (10) | 200 | $C_{15}$-alcohols (>99) |
| 12 | $iC_{14}=$ | BCPE | TFSA (1.0) HCl (0.1) | EH (25) sulfolane (10) | 167 | $C_{15}$-alcohols (>99) |
| 13 | $iC_{14}=$ | BCPE | MSA (1.0) HCl (0.1) | EH (25) sulfolane (10) | 22 | $C_{15}$-alcohols (>99) |
| 14 | $iC_{14}=$ | BBPE | MSA (1.0) HI (0.2) | EH (25) sulfolane (10) | 44 | $C_{15}$-alcohols (>99) |
| 15 | $iC_{14}=$ | BBPE | MSA (1.0) HI (0.1) | EH (25) sulfolane (10) | 100 | $C_{15}$-alcohols (>99) |
| 16 | $iC_{14}=$ | BBPE | MSA (1.0) HI (0.1) | EH (25) sulfolane (10) | 44 | $C_{15}$-alcohols (>99) |
| 17 | $1-C_8=$ | BCPE | MSA (0.5) HCl (0.2) | none | 20 | $C_9$-alcohols (90) |

We claim:

1. A process for hydroformylating olefins with carbon monoxide and a hydrogen atom source in the presence of a catalyst system comprising combining (a) a source of a Group VIII metal cation, (b) a compound acting as bidentate ligand of the formula $R^1R^2M^1$—R—$M^2R^3R^4$, wherein $M^1$ and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups, and (c) a source of anions; wherein the hydrogen atom source comprises water or a primary or secondary alcohol free of added hydrogen gas.

2. A process as claimed in claim 1 wherein the hydrogen atom source comprises water.

3. A process as claimed in claim 1, carried out at a temperature in the range of 100° to 200° C.

4. A process as claimed in claim 1, carried out with pressures in the range of 1 to 200 bar gauge.

5. A process as claimed in claim 1, wherein carbon monoxide and the hydrogen atom source are supplied in molar excess over the olefin.

6. A process as claimed in claim 1, wherein the carbon monoxide and the hydrogen atom source are supplied in a molar ratio within the range of 10:1 to 1:10.

7. A process as claimed in claim 1, wherein the Group VIII metal is a platinum group metal.

8. A process as claimed in claim 7, wherein the Group VIII metal is palladium.

9. A process as claimed in claim 1, wherein $M^1$ and $M^2$ both represent phosphorus atoms.

10. A process as claimed in claim 1, wherein the bivalent bridging group, represented by R, contains 1 to 3, carbon atoms in the bridge.

11. A process as claimed in claim 1, wherein the bivalent (substituted) group, represented by $R^1$ together with $R^2$, contains from 5 to 9, atoms.

12. A process as claimed in claim 11, wherein the bivalent (substituted) group, represented by $R^1$ together with $R^2$, is a cyclic group.

13. A process as claimed in claim 12, wherein the bivalent cyclic groups are selected from 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

14. A process as claimed in claim 11, wherein component (b) of the catalyst system is selected from the [3,3,1] and [4,2,1] isomers of 1,2-P,P'-bis(9-phosphabicyclononyl) ethane, 1,2-P,P'-bis(dimethyl-9-phosphabicyclononyl) ethane 1,3-P,P'-bis(9-phosphabicyclononyl)propane, and 1,3-P,P'-bis(dimethyl-9-phosphabicyclononyl)propane.

15. A process as claimed in claim 1, wherein acids having a pKa of less than 3, measured in aqueous solution at 18° C. are used as anion source.

16. A process as claimed in claim 15, wherein the catalyst system includes halide anions in substoichiometric amounts based on the Group VIII metal cation.

17. A process as claimed in claim 1, carried out with an olefin having 2 to 40 carbon atoms per molecule.

18. A process as claimed in claim 17, carried out with an internal olefin.

19. A process as claimed in claim 17, carried out with an in-situ prepared olefin.

20. A process as claimed in claim 19, wherein a secondary or tertiary alcohol or a precursor thereof in the form of an ester, an ether or a carbonyl compound is used as olefin source.

21. A process as claimed in claim 1, wherein carbon monoxide and a hydrogen atom source are supplied in molar excess over the olefin.

22. A process as claimed in claim 21, wherein carbon monoxide and a hydrogen atom source are supplied in a molar ratio within the range of 10:1 to 1:10.

23. A process as claimed in claim 22, wherein the Group VIII metal is a platinum group metal.

24. A process as claimed in claim 23, wherein the Group VIII metal is palladium.

25. A process as claimed in claim 23, wherein $M^1$ and $M^2$ both represent phosphorus atoms.

26. A process as claimed in claim 25, wherein the bivalent cyclic group represented by $R^1$ together with $R^2$ is selected from the group consisting of 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

27. The process as claimed in claim 26, wherein component (b) of the catalyst system is selected from the group consisting of [3,3,1] and [4,2,1] isomers of 1,2-P,P'-bis(9-phosphabicyclononyl)ethane, 1,2-P,P'-bis(dimethyl-9-phosphabicyclononyl)ethane 1,3-P,P'-bis(9-phosphabicyclononyl)propane, and 1,3-P,P'-bis(dimethyl-9-phosphabicyclononyl)ethane, 1,3-P,P'-bis(9-phosphabicyclononyl)propane, and 1,3-P,P'-bis(dimethyl-9-phosphabicyclononyl)propane.

* * * * *